(12) United States Patent
Zhu et al.

(10) Patent No.: US 8,804,106 B2
(45) Date of Patent: Aug. 12, 2014

(54) SYSTEM AND METHOD FOR NONDESTRUCTIVELY MEASURING CONCENTRATION AND THICKNESS OF DOPED SEMICONDUCTOR LAYERS

(75) Inventors: NanChang Zhu, Shanghai (CN); Derrick Shaughnessy, San Jose, CA (US); Houssam Chouaib, San Jose, CA (US); Yaolei Zheng, Shanghai (CN); Lu Yu, Shanghai (CN); Jianli Cui, Shanghai (CN); Jin An, Shanghai (CN); Jianou Shi, Palo Alto, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 13/530,774

(22) Filed: Jun. 22, 2012

(65) Prior Publication Data

US 2013/0003050 A1 Jan. 3, 2013

Related U.S. Application Data

(60) Provisional application No. 61/502,755, filed on Jun. 29, 2011.

(51) Int. Cl.
*G01N 21/00* (2006.01)
*G01B 11/28* (2006.01)

(52) U.S. Cl.
USPC .............................................. 356/73; 356/630

(58) Field of Classification Search
USPC ......................................................... 356/630
See application file for complete search history.

(56) References Cited

U.S. PATENT DOCUMENTS

| | | | | |
|---|---|---|---|---|
| 5,042,952 | A | * | 8/1991 | Opsal et al. .................... 356/432 |
| 6,242,739 | B1 | * | 6/2001 | Cherkassky ............. 250/339.11 |
| 6,268,916 | B1 | * | 7/2001 | Lee et al. ........................ 356/369 |
| 2004/0085538 | A1 | * | 5/2004 | Hovinen et al. ............... 356/369 |
| 2007/0188761 | A1 | * | 8/2007 | Salnik et al. .................... 356/432 |
| 2008/0151247 | A1 | * | 6/2008 | Salnik et al. .................... 356/432 |

* cited by examiner

*Primary Examiner* — Gregory J Toatley
*Assistant Examiner* — Hina F Ayub
(74) *Attorney, Agent, or Firm* — Suiter Swantz pc llo

(57) ABSTRACT

The disclosure is directed to nondestructive systems and methods for simultaneously measuring active carrier concentration and thickness of one or more doped semiconductor layers. Reflectance signals may be defined as functions of active carrier concentration and thickness varying over different wavelengths and over different incidence angles of analyzing illumination reflected off the surface of an analyzed sample. Systems and methods are provided for collecting a plurality of reflectance signals having either different wavelengths or different incidence angle ranges to extract active carrier density and thickness of one or more doped semiconductor layers.

23 Claims, 4 Drawing Sheets

SYSTEM AND METHOD FOR NONDESTRUCTIVELY MEASURING CONCENTRATION AND THICKNESS OF DOPED SEMICONDUCTOR LAYERS

PRIORITY

The present application claims priority to U.S. Provisional Application Ser. No. 61/502,755, entitled NON-DESTRUCTIVE METHOD FOR SIMULTANEOUS MEASUREMENTS OF CONCENTRATION AND THICKNESS ON N OR P DOPED SEMICONDUCTOR LAYERS, Chouaib et al., filed Jun. 29, 2011, which is currently co-pending, or is an application of which a currently co-pending application is entitled to the benefit of the filing date.

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure generally relates to the field of semiconductor metrology and more particularly to a system and method for nondestructively measuring thickness and active carrier concentration of doped semiconductor layers.

BACKGROUND

Current trends in the manufacture of electronic devices require semiconductors to be fabricated on smaller scales without sacrificing performance or capabilities. Inspecting or measuring semiconductor wafer attributes during the fabrication process may be preferred because an electronic system or device may not function properly if it includes a semiconductor that has not been fabricated within sometimes delicate specifications. Therefore, several optical metrology techniques may be utilized to measure spatial and/or physical attributes of semiconductor wafers at various stages in the fabrication process to ensure proper performance of a finished product.

For example, certain applications require tight control of thickness and active carrier concentration of doped semiconductor layers, such as P-doped, N-doped layers and the like. Accordingly, it may be necessary to extract information about both thickness and active carrier concentration of a doped layer of a semiconductor wafer at various stages of the semiconductor fabrication process. In addition, nondestructive measurement techniques may be necessary to ensure the semiconductor wafer does not sustain damage causing the fabricated semiconductor to function improperly.

Commercially suitable technologies are not yet available for simultaneously extracting thickness and active carrier concentration from reflectance signals without one of thickness or active carrier concentration being known. Several current technologies, such as those disclosed in Clarysse et al., J. Vac. Sci. Technol. B24(3) 1139 (2006), Bogdanowicz et al., J. Vac. Sci. Technol. B26(1) 310 (2008), and Bogdanowicz et al., J. Applied Phys. 108, 104908 (2010), require unduly complicated modeling and excessive data processing. Other methods of measurement, such as secondary ion mass spectroscopy (SIMS) or scanning spreading resistance microscopy (SSRM), may cause destructive interaction with the semiconductor wafer. Thus, they are also inappropriate measurement techniques for wafers destined for semiconductor fabrication.

SUMMARY

The present disclosure is directed to systems and methods for simultaneously performing nondestructive thickness and active carrier concentration measurements of a doped semiconductor layer.

In one aspect, the present disclosure is directed to a system for measuring thickness and active carrier concentration of a doped semiconductor layer, including: a pump source configured to inject charge carriers into a region of a sample to enhance index contrast between a doped layer of the sample and a substrate of the sample; one or more probe sources configured to illuminate a surface of the sample proximate to the injected region of the sample with illumination having a first wavelength and illumination having at least one additional wavelength; one or more detectors further configured to detect illumination of the first wavelength reflected from the surface of the sample, the one or more detectors further configured to detect illumination of at least one additional wavelength reflected from the surface of the sample; and one or more computing systems communicatively coupled to the one or more detectors, the one or more computing systems configured to: acquire information associated with reflected illumination having the first wavelength from the one or more detectors, acquire information associated with reflected illumination having at least one additional wavelength from the one or more detectors, compare information associated with reflected illumination having the first wavelength and information associated with reflected illumination having at least one additional wavelength, and determine active carrier concentration and thickness of the doped layer of the sample utilizing the comparison of information associated with reflected illumination having the first wavelength and information associated with reflected illumination having at least one additional wavelength.

In another aspect, the present disclosure is directed to a method for measuring thickness and active carrier concentration of a doped semiconductor layer, including the steps of: injecting charge carriers into a region of a sample to enhance index contrast between a doped layer of the sample and a substrate of the sample; illuminating a surface of the sample proximate to the injected region of the sample with illumination having a first wavelength; illuminating the surface of the sample proximate to the injected region of the sample with illumination having at least one additional wavelength; detecting illumination of the first wavelength reflected from the surface of the sample; detecting illumination of at least one additional wavelength reflected from the surface of the sample; acquiring information associated with reflected illumination having the first wavelength; acquiring information associated with reflected illumination having at least one additional wavelength; comparing information associated with reflected illumination having the first wavelength and information associated with reflected illumination having at least one additional wavelength; and determining active carrier concentration and thickness of the doped layer of the sample utilizing the comparison of information associated with reflected illumination having the first wavelength and information associated with reflected illumination having at least one additional wavelength.

In another aspect, the present disclosure is directed to a system for measuring thickness and active carrier concentration of a doped semiconductor layer, including: a pump source configured to inject charge carriers into a region of a sample to enhance index contrast between a doped layer of the sample and a substrate of the sample; a probe source configured to illuminate a surface of the sample proximate to the injected region of the sample; one or more masks configured to allow a first portion of illumination having a first range of incidence angles relative to the surface of the sample, the one or more masks further configured to allow at least one additional portion of illumination having at least one additional range of incidence angles relative to the surface of the sample; one or more detectors configured to detect the first portion of illumination reflected from the surface of the sample having the first range of incidence angles, the one or more detectors further configured to detect at least one additional portion of illumination reflected from the surface of the sample having at least one additional range of incidence angles; and one or more computing systems communicatively coupled to the one or more detectors, the one or more computing systems configured to: acquire information associated with the first portion of illumination having the first range of incidence angles from the one or more detectors, acquire information associated with at least one additional portion of illumination having at least one additional range of incidence angles from the one or more detectors, compare information associated with first portion of illumination having the first range of incidence angles and information associated with at least one additional portion of illumination having at least one additional range of incidence angles, and determine active carrier concentration and thickness of the doped layer of the sample utilizing the comparison of information associated with first portion of illumination having the first range of incidence angles and information associated with at least one additional portion of illumination having at least one additional range of incidence angles.

In another aspect, the present disclosure is directed to a method for measuring thickness and active carrier concentration of a doped semiconductor layer, including the steps of: injecting charge carriers into a region of a sample to enhance index contrast between a doped layer of the sample and a substrate of the sample; illuminating a surface of the sample proximate to the injected region of the sample; allowing a first portion of illumination having a first range of incidence angles relative to the surface of the sample; allowing at least one additional portion of illumination having at least one additional range of incidence angles relative to the surface of the sample; detecting the first portion of illumination reflected from the surface of the sample having the first range of incidence angles; detecting at least one additional portion of illumination reflected from the surface of the sample having at least one additional range of incidence angles; acquiring information associated with the first portion of illumination having the first range of incidence angles; acquiring information associated with at least one additional portion of illumination having at least one additional range of incidence angles; comparing information associated with first portion of illumination having the first range of incidence angles and information associated with at least one additional portion of illumination having at least one additional range of incidence angles; and determining active carrier concentration and thickness of the doped layer of the sample utilizing the comparison of information associated with first portion of illumination having the first range of incidence angles and information associated with at least one additional portion of illumination having at least one additional range of incidence angles.

In another aspect, the present disclosure is directed to a method for measuring thickness and damage profile of at least one semiconductor layer, including the steps of: injecting charge carriers into a region of a sample to enhance index contrast between at least one layer of the sample and a substrate of the sample; illuminating a surface of the sample proximate to the injected region of the sample with illumination having a first wavelength; illuminating the surface of the sample proximate to the injected region of the sample with illumination having at least one additional wavelength; detecting illumination of the first wavelength reflected from the surface of the sample; detecting illumination of at least one additional wavelength reflected from the surface of the sample; acquiring information associated with reflected illumination having the first wavelength; acquiring information associated with reflected illumination having at least one additional wavelength; comparing information associated with reflected illumination having the first wavelength and information associated with reflected illumination having at least one additional wavelength; and determining thickness and a damage level of the at least one layer of the sample utilizing the comparison of information associated with reflected illumination having the first wavelength and information associated with reflected illumination having at least one additional wavelength.

In another aspect, the present disclosure is directed to a method for measuring thickness and damage profile of at least one semiconductor layer, including the steps of: injecting charge carriers into a region of a sample to enhance index contrast between at least one layer of the sample and a substrate of the sample; illuminating a surface of the sample proximate to the injected region of the sample; allowing a first portion of illumination having a first range of incidence angles relative to the surface of the sample; allowing at least one additional portion of illumination having at least one additional range of incidence angles relative to the surface of the sample; detecting the first portion of illumination reflected from the surface of the sample having the first range of incidence angles; detecting at least one additional portion of illumination reflected from the surface of the sample having the at least one additional range of incidence angles; acquiring information associated with the first portion of illumination having the first range of incidence angles; acquiring information associated with the at least one additional portion of illumination having the at least one additional range of incidence angles; comparing information associated with the first portion of illumination having the first range of incidence angles and information associated with the at least one additional portion of illumination having the at least one additional range of incidence angles; and determining thickness and a damage level of the at least one layer of the sample utilizing the comparison of information associated with first portion of illumination having the first range of incidence angles and information associated with the at least one additional portion of illumination having the at least one additional range of incidence angles.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

FIGS. 1 through 4 generally illustrate systems and methods for nondestructively performing simultaneous measurements of thickness and active carrier concentration of a doped layer of a wafer utilizing direct current (DC) reflectance and/or modulated optical reflectance (MOR) signals. The refractive index of a doped layer tends to increase or decrease in response to change in dopant concentration. Reflectance signals carry interference information associated with refractive index contrast between the doped layer and the underlying substrate. Thus MOR and/or DC reflectance signals may include information associated with thickness of the doped layer and active carrier concentration (i.e. the electrically active dopant concentration). The present disclosure is accordingly directed to robust commercially-suitable systems and methods for simultaneously extracting thickness and active carrier concentration of one or more doped layers of a wafer from a plurality of reflectance signals measured at different wavelengths and/or different incidence angles.

As used throughout the present disclosure, the terms "sample" or "wafer" generally refer to any substrate formed of a semiconductor or non-semiconductor material. For example, semiconductor or non-semiconductor materials include, but are not limited to, monocrystalline silicon, gallium arsenide, and indium phosphide. A wafer may include one or more layers. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

As used throughout the present disclosure, the term "optical path" generally refers to any path along which illumination can travel, such as free space defining a line of sight between two points. In various embodiments, one or more optical paths may include a path defined by a configuration of one or more optical elements including, but not limited to, optical fibers, couplers, crystals, imaging lenses, glass plates, glass cubes, diffractive elements, retarders, quarter wave plates, focus optics, phase modulators, polarizers, mirrors, beam splitters, reflectors, converging/diverging lenses, prisms, or any other optical elements disclosed herein. Those skilled in the art will appreciate that an optical path may have many alternate configurations, all capable of accomplishing the same result of directing portions of illumination to one or more designated destinations. Therefore, the embodiments described herein are only included for illustrative purposes and should not be construed as limitations on the present disclosure.

Figure 1:
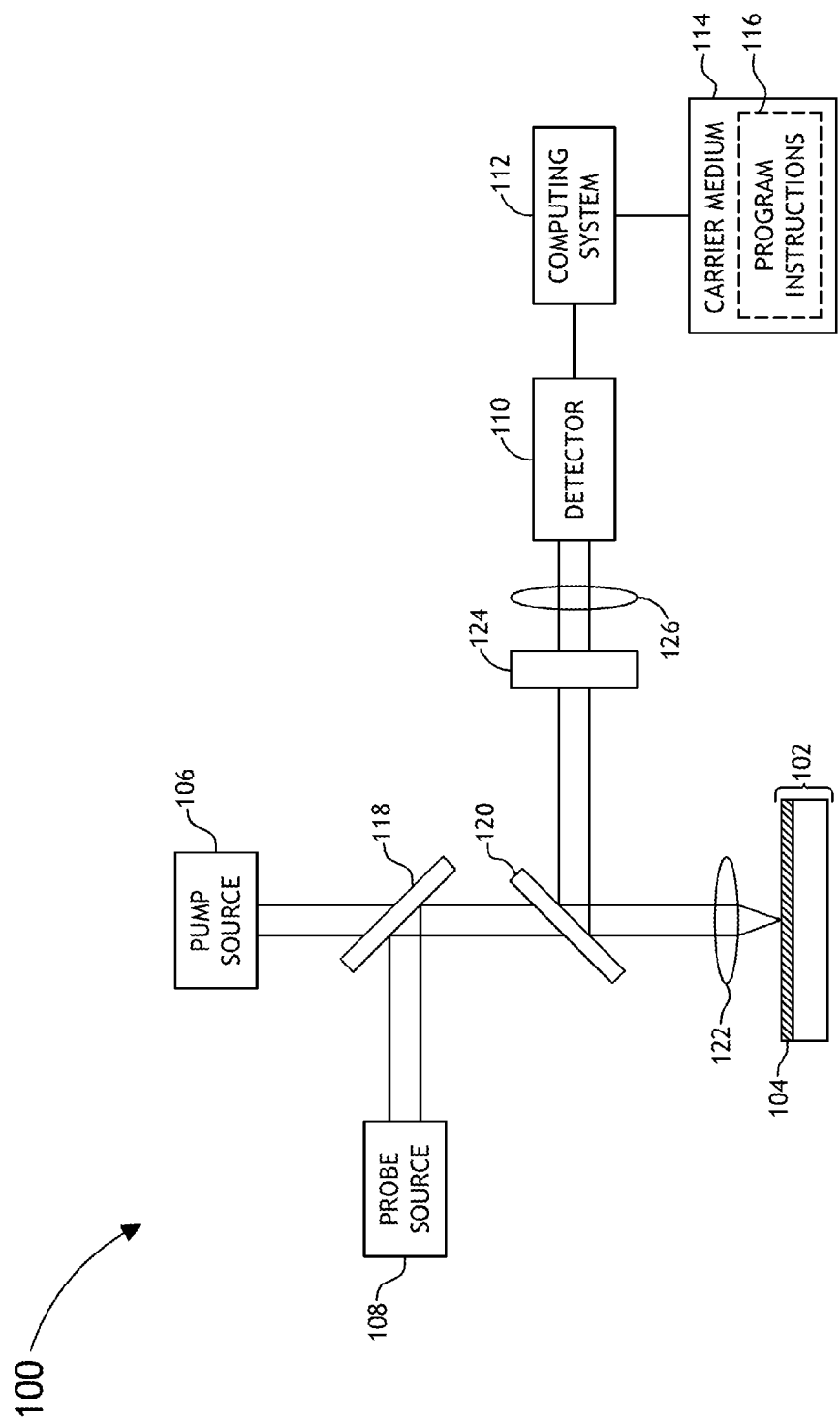
FIG. 1 is a block diagram illustrating a system for measuring thickness and active carrier concentration of a doped semiconductor layer.
Figure 2:
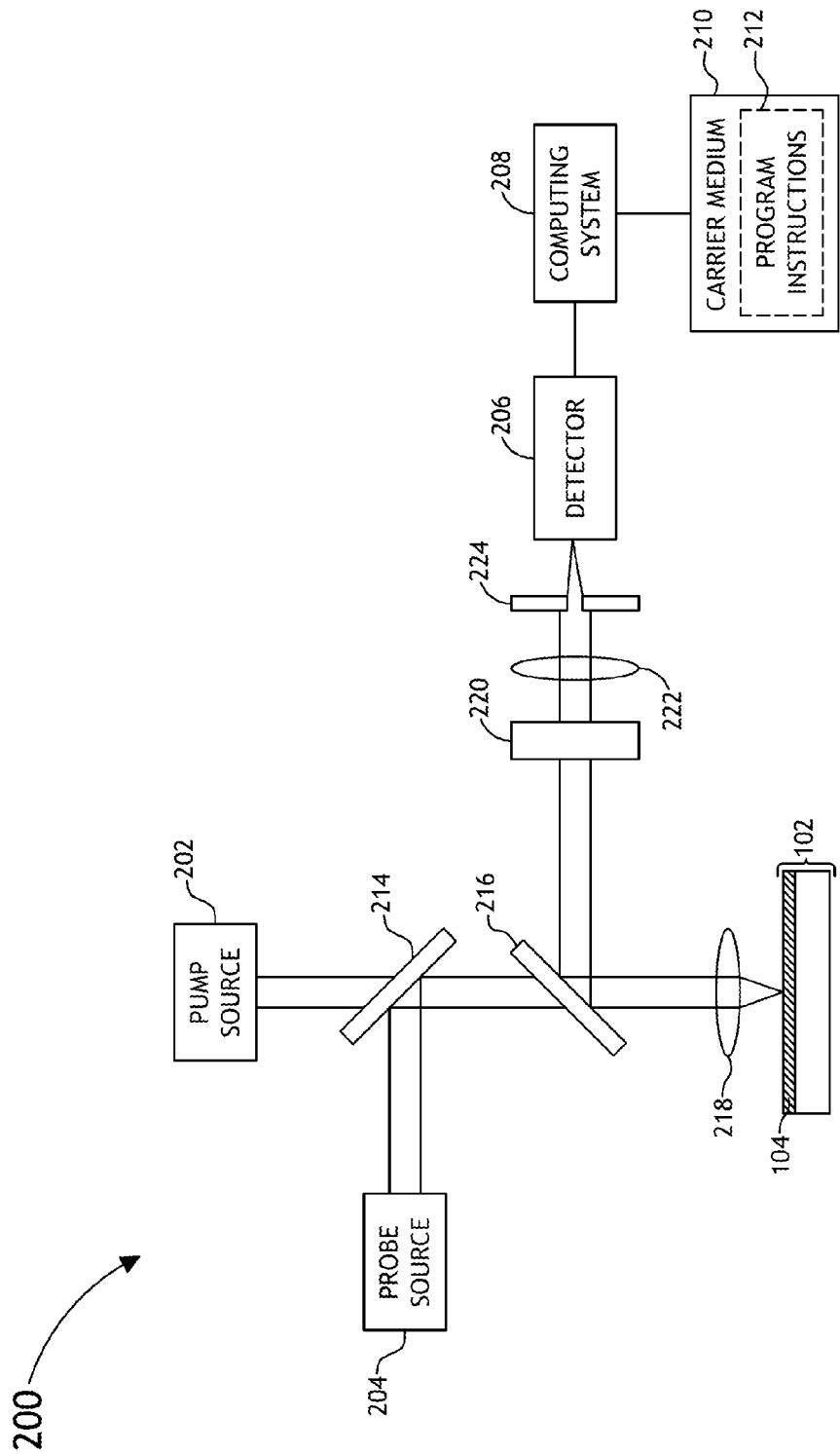
FIG. 2 is a block diagram illustrating a system for measuring thickness and active carrier concentration of a doped semiconductor layer.

FIGS. 1 and 2 illustrate alternative systems for simultaneously measuring thickness and active carrier concentration of at least one doped semiconductor layer of a sample 102. The sample 102 may include one or more doped layers 104, such as P-doped or N-doped layers of semiconductive media.

In an embodiment including a plurality of doped layers, each layer 104 may have unique values for active carrier concentration and/or thickness. Thus, while the present disclosure may describe measuring thickness and active carrier concentration with respect "a", "one", or "the" doped layer throughout much of the description; the systems and methods disclosed herein should nevertheless be understood to extend to multiple-layer applications and should not be limited to taking measurements of a single doped layer.

It is noted herein that measuring active carrier concentration may have advantages over simply measuring dopant concentration because active carrier concentration tends to have a closer relationship with physical properties of the doped layer 104, such as conductivity, reflectivity, refractive index, and the like. However, it is further contemplated that stoichiometric dopant concentration or any other measure of doping level may be obtained utilizing systems and/or methods described herein. As such, the term active carrier concentration should be construed to include all such measurements unless otherwise noted. Furthermore, the term "thickness" as used herein may refer to junction depth or any other spatial parameter tending to affect one or more physical properties of the doped layer 104.

FIG. 1 illustrates a system 100 for measuring thickness and active carrier concentration of the doped layer 104 of the sample 102 utilizing a plurality of reflectance signals measured at two or more different wavelengths. Reflectance may be modeled as a function of refractive index and thickness of the doped layer 104. In addition, refractive index of the doped layer 104 may be modeled as a function of wavelength of reflected illumination and active carrier concentration. Accordingly, reflectance signals generated from illumination reflected off a surface of the sample 102 may be analyzed as functions of thickness and active carrier concentration of the doped layer 104 and wavelength of reflected illumination. The signals may be modeled utilizing appropriate mathematical models, such as a combination of one or more of reflection interference modeling, Drude modeling of refractive index perturbations caused by charge carriers, Soref modeling of absorption coefficient perturbations produced by charge carriers, and/or any other mathematical models or combination of models known to the art for defining reflectance as a function of thickness and active carrier concentration of the doped layer 104 and wavelength of reflected illumination. In depth descriptions and discussions of various models and principles recited herein are provided in Burstein et al., Phys. Rev. 93, 632 (1954) and Soref et al., IEEE Journal of Quantum Electronics, Vol. QE-23, 123 (1987), both fully incorporated herein by reference.

The system 100 may include a pump source 106 configured to inject charge carriers, such as photo carriers, into a region of the sample 102, such as a portion of the doped layer 104 from which measurements are being drawn. Exciting the region of the sample 102 with the injected charge carriers may create thermal waves or carrier-density modulation to affect reflective properties of the sample. In addition, the injected charge carriers may enhance index contrast between the doped layer 104 and an underlying substrate of the sample 102 so that there is an increased difference between refractive index of the doped layer 104 and refractive index of the substrate. The increased difference between refractive index of the doped layer 104 and refractive index of the substrate may produce detectable interference in reflectance signals collected from illumination reflected off the surface of the sample 102. The detectability of interference in the reflectance signals resulting from index contrast allows information associated with active carrier density of the doped layer 104 to be extracted from a plurality of reflectance signals measured at different wavelengths utilizing the previously mentioned relationship between refractive index and active carrier density and wavelength. For example, reflectance signals measured at two or more wavelengths may be compared to determine active carrier concentration of the doped layer 104 as a unique solution for refractive index extracted from the measured reflectance values analyzed over an ascertainable variable, such as power, intensity, phase, amplitude, in-phase and quadrature components or any other ascertainable variable for comparing reflectance signals to extract information associated with refractive index.

The pump source 106 may include at least one illumination source configured to provide illumination at one or more discrete power levels or in a continuous range of power levels to excite the region of the sample 102 with charge carriers. The pump source 106 may be further configured to provide intensity modulated illumination at a predetermined frequency to excite the region of the sample 102, as described in U.S. Pat. No. 7,502,104 incorporated herein by reference. In one embodiment, the pump source 106 may include at least one single-wavelength illumination source, such as a gas, solid state, or semiconductor laser. In another embodiment, the pump source 106 may include at least one broadband (i.e. multiple-wavelength) illumination source, such as a Xenon arc lamp, a super continuum laser, or a laser sustained plasma source. It is further contemplated that the pump source 106 could include other sources of electromagnetic radiation to excite the region of the sample 102 and to enhance index contrast between the doped layer 104 and the substrate. For example, it is contemplated that the pump source 106 could include electron or particle beams to inject the excited region with electrons or other charge carriers.

The system 100 may further include at least one probe source 108 configured to illuminate a portion of the surface of the sample 102 proximate to the excited region of the doped layer 104. The probe source 108 may include one or more single-wavelength or broadband illumination sources configured to illuminate the portion of the surface of the sample 102 with illumination having a plurality of different wavelengths. For example, the probe 108 source may include a first illumination source configured to illuminate the surface of the sample 102 with illumination having a first wavelength. The probe source 108 may further include one or more additional illumination sources configured to illuminate the surface of the sample 102 with illumination having one or more additional wavelengths. Alternatively, the probe source 108 may include a single illumination source configured to illuminate the surface of the sample with illumination having two or more wavelengths. For example, the single illumination source may be configured to provide illumination at two or more selectable or tunable wavelengths. The probe source 108 may be further configured to provide illumination at two or more wavelengths simultaneously or to provide illumination at one wavelength at a time.

The system 100 may further include at least one detector 110 configured to receive illumination reflected off the surface of the sample 102. The detector 110 may include one or more of any illumination detectors known to the art, such as photodiodes, photo resistors, CCD cameras, CMOS cameras, two dimensional arrays, linear arrays, and the like. The detector 110 may be configured to detect at least a portion of reflected illumination originating from the pump source 106 or from the probe source 108. Alternatively, the detector 110 may be configured to receive illumination originating from both the pump source 106 and the probe source 108. The detector 110 may be further configured to receive reflected illumination at two or more different wavelengths. For example, the detector 110 may be configured to receive a first portion of reflected illumination having a first wavelength and further configured to receive at least one additional portion of reflected illumination having a different wavelength.

In one embodiment, the system 100 may include one or more optical paths defined by a plurality of optical elements to define the flow of illumination emanating from the pump and/or probe sources 106 and 108. For example, the system may include a beam splitter/combiner 118 configured to receive illumination emanating from the pump source 106 and illumination emanating from the probe source 108. The splitter/combiner 118 may combine two or more beams of illumination from the pump and probe sources 106 and 108 and direct the combined beams through a focusing lens 122 to a measurement location on the surface of the sample 102. The pump illumination received at the measurement location may excite the underlying region of the sample including a portion of the doped layer 104 to inject charge carriers. In addition, the pump illumination, if modulated, may create thermal waves or carrier-density modulation in the doped layer 104.

The system 100 may further include an additional beam splitter/combiner 120 configured to receive at least a portion of pump and/or probe illumination reflected from the surface of the sample 102. The splitter/combiner 120 may be further configured to direct a portion of the reflected illumination along a delivery path to the detector 110. The delivery path may include an optical filter 124 configured to block either pump or probe illumination so that only illumination originating from one of the sources is allowed. The optical filter 124 may be alternatively configured to only allow illumination having a specified wavelength or range of wavelengths. Otherwise, the system may exclude the optical filter 124 or the optical filter 124 may allow both pump and probe illumination to pass through while blocking out other unwanted illumination. The delivery path may further include a focusing lens 126 configured to focus illumination directed to the detector 110.

In one embodiment, the system 100 may further include one or more diffractive elements, such as beam splitters, gratings, prisms or other optical elements configured to direct portions of reflected illumination along a plurality of delivery paths to a plurality of detectors 110. The one or more diffractive elements may be further configured to direct different portions of reflected illumination along different delivery paths based on wavelength, such that two or more portions of illumination having different wavelengths from each other are directed each directed along a different path to a corresponding detector 110. It is contemplated that the plurality of paths may be utilized to normalize measurements by monitoring the plurality of corresponding detectors 110 for information associated with incident beams.

In one embodiment, the system 100 may further include polarizing elements disposed along one or more of the optical paths configured for performing optical metrology. The polarizing elements may be fixed, adjustable, or rotating. The polarizing elements may be configured for detection of additional characteristics of reflected illumination to allow improved measurement results of the overall system. For example, the polarizing elements may be configured for making spatial measurements of the sample. The corresponding metrology data may be forward-fed to aid subsequent thickness and active carrier concentration measurements. Alternatively, the corresponding metrology data may be back-fed to condition previous thickness and active carrier concentration measurements.

The system 100, may further include one or more computing systems 112 communicatively coupled to the pump source 106, the probe source 108, and/or the detector 110. The one or more computing systems 112 may be configured to execute program instructions 116 from carrier media 114 to control the pump source 106 and/or the probe source 108. For example, the one or more computing systems 112 may execute program instructions 116 to control tunable aspects of the illumination sources of the pump and probe sources 106 and 108, such as adjusting power level, illumination intensity, wavelength, modulation frequency, and the like.

In one embodiment, at least one computing system 112 may be communicatively coupled to the detector 110. The computing system 112 may be configured to acquire reflectance information associated with at least a portion of reflected illumination received by the detector 110, such as in-phase and/or quadrature components, amplitude, phase, wavelength, frequency, and the like. The computing system 112 may be further configured to acquire reflectance information associated with at least two portions of reflected illumination having different wavelengths. For example, the computing system 112 may be configured to acquire a first reflectance signal associated with a first portion of reflected illumination having a first wavelength. The computing system 112 may be further configured to, simultaneously or subsequently, receive at least one additional reflectance signal associated with an additional portion of illumination having a different wavelength from the first. The same detector may be configured to detect the additional portion of illumination. Alternatively a plurality of detectors 110 may be employed, each configured to detect a different portion of illumination.

The computing system 112 may be further configured to compare reflectance signals associated with two or more portions of detected illumination having different wavelengths. The computing system 112 may be further configured to determine active carrier concentration and thickness of the doped layer 104 of the sample 102 utilizing the comparison of two or more reflectance signals measured at two or more different wavelengths. For example, the computing system 112 may be configured to compare the plurality of reflectance signals utilizing an appropriate mathematical model for defining reflectance as a function of active carrier concentration, and wavelength. The computing system 112 may be configured to determine unique solutions for thickness and active carrier concentration of the plurality of reflectance signals. Accordingly, the computing system 112 may be configured to execute such an algorithm from program instructions 116 embodied in carrier media, such as a permanent or semi-permanent memory storage device, to extract thickness and active carrier concentration measurements of the doped layer 104 of the sample 102 from two or more reflectance signals.

In a further embodiment, the reflectance signals may include DC reflectance or MOR signals. Alternatively, the computing system 112 may be configured to utilize a combination of DC reflectance and MOR signals acquired from the detector 110 to determine thickness and active carrier concentration. For example, in one embodiment the computing system 112 may be configured to determine one or more calibration values for active carrier concentration and thickness for a doped layer 104 of a calibration sample 102 utilizing MOR signals and an appropriate mathematical model. The computing system 112 may be further configured to determine active carrier concentration and thickness of one or more doped layers 104 of experimental samples 102 utilizing DC reflectance signals and the calibration values to reduce error. The DC reflectance signals may be easier to process and may generally require less complex models then MOR signals; however, calibration with MOR signals may improve accuracy.

In one embodiment the computing system 112 may be further configured to acquire information associated with a DC reflectance signal and an MOR signal processed by at least one of a hardware or software filter to extract information of associated with at least one excitation frequency at which excess charge carriers are generated. The computing system 112 may be further configured to extract information associated with harmonics of the excitation frequency. The computing system 112 may be further configured to extract amplitude and phase of the MOR signal. Alternatively, the computing system 112 may be configured to extract in-phase and quadrature components of the MOR signal. The computing system 112 may be further configured to normalize at least one of the AC components (e.g. amplitude, in-phase, and/or quadrature) of the MOR signal utilizing the DC reflectance signal. The computing system 112 may be further configured to compare two or more normalized MOR signals corresponding to different wavelengths to extract active carrier concentration and thickness measurements of the doped layer 104.

In one embodiment, the computing system 112 may be further configured to determine active carrier concentration and thickness of the doped layer 104 of the sample 102 utilizing reflectance signals measured from illumination beams having incremental separation to scan a region of the sample 102. The pump and/or probe source 106 and/or 108 may be configured to illuminate a region of the surface of the sample 102. The probe source 108 may include an actuation arm configured to actuate the illumination source of the probe source 108 in response to beam location of the pump source 106 to incrementally scan the regions excited by the pump source 106. Alternatively, the pump source 106 may include an actuation arm configured to actuate the illumination source of the pump source 106 in response to beam location of the probe source 108 to incrementally excite regions illuminated by the probe source 108. In one embodiment, both the pump and probe sources 106 and 108 may include actuation means configured to actuate illumination sources of the pump and probe sources 106 and 108 to provide incrementally separated illumination beams to one or more portions of the surface of the sample 102. The computing system 112 may be further configured to determine active carrier concentration and thickness of the doped layer 104 of the sample 102 utilizing reflectance signals associated with two or more wavelengths collected by the detector 110 from incrementally separated measurement locations of the scanned regions. For example, the computing system 112 may be configured to determine active carrier concentration and thickness of the doped layer 104 utilizing DC reflectance scans collected at two or more probe wavelengths.

In one embodiment, the computing system 112 may be further configured to determine active carrier concentration and thickness utilizing data conditioning algorithms to process reflectance measurements. For example, the computing system 112 may utilize linear regression, non-linear regression, library optimization, or other data conditioning techniques known to the art to reduce discrepancies between measured values and modeled values.

FIG. 2 illustrates a system 200 for measuring thickness and active carrier concentration of the doped layer 104 of the sample 102 utilizing a plurality of reflectance signals measured at two or more different incidence angles or ranges of incidence angles. The foregoing discussion of system 100 and its various elements and aspects shall also apply to system 200 unless otherwise noted herein. Similarly, the following discussion of system 200 and its various elements and aspects shall apply to system 100 unless otherwise noted herein. For example, the foregoing description of a "pump source", "probe source", "detector", and any other element included in both systems 100 and 200 shall carry throughout the present disclosure. In addition, any elements of system 100 and system 200 may be combined into a single system. Therefore, the inclusion or exclusion of various elements in the presently disclosed embodiments of system 100 and system 200 is exemplary and should not be construed to limit either system in any way.

System 200 relies on modeling reflectance as a function of active carrier concentration and thickness of the doped layer 104 of the sample 102 varying over different ranges of incidence angles. An incidence angle may refer to an angle made by a portion of illumination intersected the surface of the sample 102 or an angle made by a portion of illumination reflected off the surface of the sample 102. Accordingly, the system 200 may allow extraction of active carrier concentration and thickness measurements for the doped layer 104 of the sample 102 from two or more reflectance signals measured at different incidence angle ranges. For example, the active carrier concentration and thickness of the doped layer 104 may be found as a unique solution, such as a common value, of the two or more reflectance signals.

The system 200 may include a pump source 202 configured to excite a region of the sample 102 including a portion of the doped layer 104 to generate charge carriers. The pump source 202 may be intensity modulated such that the charges carriers have a time varying density. Accordingly, the pump source 202 may generate thermal waves or carrier-density modulation in the doped layer 104. For example, the pump source 202 may include an intensity modulated illumination source configured to illuminate a portion of the surface of the sample 102 with illumination provided at a predetermined frequency sufficient for creating thermal waves or carrier-density modulation in the sample 102, such as a frequency in the range of 0.01 to 100 Megahertz. The pump source 202 may further provide illumination to excite a region of the sample 102 at one or more discrete power levels or in a continuous range of power levels.

The system 200 may further include a probe source 204 configured to illuminate a portion of the surface of the sample 102 including at least one measurement location. The probe source 204 may include a single-wavelength, multiple single wavelength sources, or a broadband illumination source configured to provide illumination at one or more power levels. The system may further include a focusing lens 218 disposed between the probe source 204 and the sample 102. The focusing lens 218 may be configured to create a spread of incidence angles in illumination directed from the probe source 204 to the sample 102.

The system 200 may further include at least one detector 206 configured to receive at least a portion of reflected illumination from the surface of the sample 102. The detector 206 may be further configured to receive two or more portions of illumination, each portion having a different range of incidence angles.

The system 200 may further include one or more optical paths defined by other optical elements. For example, the system 200 may include a beam combiner 214 configured to receive pump and probe illumination beams. The combiner 214 may be further configured to direct the pump and probe beams through the focusing lens 218 to the surface of the sample 102. The system 200 may further include a beam splitter 216 configured to receive illumination reflected from the surface of the sample 102. The splitter 216 may be further configured to direct at least a portion of the reflected illumination to the detector 206 along a delivery path. The system 200 may further include various optical elements disposed along the delivery path, such as an optical filter 220 configured to block undesired illumination and/or a focusing lens 222 configured to focus illumination at the detector 206. The system 200 may further include additional elements as needed. For example, in one embodiment the system 200 may further include a relay lens disposed along the delivery path configured for imaging the pupil plane of the focusing lens 218 onto the detector plane.

The system 200 may further include one or more optical masks 224 configured to block at least a portion of reflected illumination from reaching the detector 206. The mask 224 may be further configured to allow at least a portion of reflected illumination having a desired range of incidence angles to be received by the detector 206. The mask 224 may be disposed between the sample 102 and the detector 206 and configured to only allow a portion of reflected illumination directed along the delivery path having a desired range of incidence angles to reach the detector 206. For example, the mask 224 may be disposed along the delivery path just prior to the detector as illustrated in FIG. 2. Alternatively, the mask 224 may be disposed between the probe source 204 and the sample 102 and configured to only allow a portion of illumination supplied by the probe source 204 to reach the sample 102, thereby limiting the range of incidence angles present in illumination reflected off the surface of the sample 102.

In one embodiment, the mask 224 may include one or more apertures having fixed spatial parameters, such as a fixed radius. The fixed aperture may be configured to allow only illumination having a fixed range of incidence angles to pass through the aperture while blocking all illumination falling outside of the range. For example, the system 200 may include one or more masks 224 each including at least one fixed aperture configured to allow illumination having a different range of incidence angles. Accordingly, a first mask 224 may be configured to allow first portion of illumination having a first range of incidence angles to reach the detector 206. The detector 206 may be further configured to detect an additional portion of illumination having a different range of incidence angles either by removal of the first mask 224 or by utilizing one or more additional masks 224 configured to allow at least one additional portion of illumination having a different range of incidence angles to reach the detector.

In another embodiment, the mask 224 may include at least one aperture having adjustable spatial parameters configured to allow illumination having a desired range of incidence angles to pass through the aperture. Accordingly, the adjustable aperture may be sequentially adjusted to detect at least two different portions of illumination having different incidence angle ranges from each other.

The mask 224 is not limited to an aperture and may alternatively encompass any device known to the art for limiting the range of incidence angles present in illumination received by one or more detectors 206. For example, the mask 224 may include one or more diffractive optical elements, such as a beam splitter, a micro-mirror assembly, a grating, a prism, or any other optical element or device configured to direct portions of illumination having different ranges of incidence angles or azimuthal angles along different optical paths.

In one embodiment, the mask 224 may include one or more diffractive elements configured to direct a first portion of reflected illumination having a first range of incidence angles along a first path to the detector 206. The detector 206 may be further configured to detect at least one additional portion of illumination having a different range of incidence angles by removal of the mask 224, actuation of the mask 224 to allow a different diffractive effect, or utilization of at least one different diffractive element. In another embodiment, one or more diffractive elements may be configured to direct two or more portions of illumination having different incidence angle ranges along two or more different optical paths. Two or more detectors 206 may be configured to each receive a different portion of illumination from the plurality of different optical paths. Accordingly, the two or more detectors 206 may simultaneously or sequentially detect two or more portions of illumination having different ranges of incidence angles from each other.

In one embodiment, the mask 224 may be further configured to direct portions of reflected illumination having different incidence or reflection angles relative to a reference plane (hereinafter "azimuthal angles") along different optical paths to one or more detector 206. Different detectors 206 or different regions of a detector 206 may be configured to receive different portions of reflected illumination having different azimuthal angles. For example, the detector 206 may include a quad cell photodiode configured as follows: Cell 1 (azimuth 0 & angle of incidence range ("AOI") #1), Cell 2 (azimuth 90 and AOI #1), Cell 3 (azimuth 180 and AOI #2), Cell 4 (azimuth 270 and AOI #2). The foregoing example is only included for illustrative purposes and should not be construed to limit the present disclosure in any way.

In a further embodiment, the mask 224 may be configured to actuate (e.g. rotate or translate) such that different portions of the detector 206 or different detectors 206 receive different portions of reflected illumination having different incidence angle ranges having the same azimuth. The mask 224 may be further configured to synchronize its motion with the detector 206 so that incidence angle and azimuth information may be collected more rapidly.

The system 200 may further include at least one computing system 208 communicatively coupled to the one or more detectors 206. The computing system 208 may be configured to acquire reflectance information associated with each of two or more portions of illumination having different incidence angle ranges. The computing system 208 may be further configured to execute an algorithm from program instructions 212 on carrier media 210 to compare reflectance signals corresponding to the two or more portions of illumination having different incidence angle ranges. The computing system 208 may be further configured to determine active carrier concentration and thickness of the doped layer 104 of the sample 102 utilizing information extracted from comparison of the two or more reflectance signals associated with different incidence angle ranges.

In one embodiment, the computing system 208 may be configured to compare a first MOR signal associated with a first range of incidence angles and at least one additional MOR signal associated with a different range of incidence angles. The computing system 208 may be further configured to determine active carrier concentration and thickness of the doped layer 104 of the sample 102 utilizing a unique solution of the compared MOR signals. Active carrier concentration and thickness may be extracted from a unique solution of two or more MOR signals because MOR signal amplitude is proportional to active carrier concentration and the signal shape is generally a function of thickness. Accordingly, the computing system 208 may be configured to utilize MOR models known to the art to compare the two or more MOR signals to find a unique solution for active carrier concentration and thickness of the doped layer 104 of the sample 102.

The computing system 208 may be further configured to utilize data conditioning techniques, such as those previously discussed for system 100, to improve accuracy or precision of the measurements.

Figure 3:
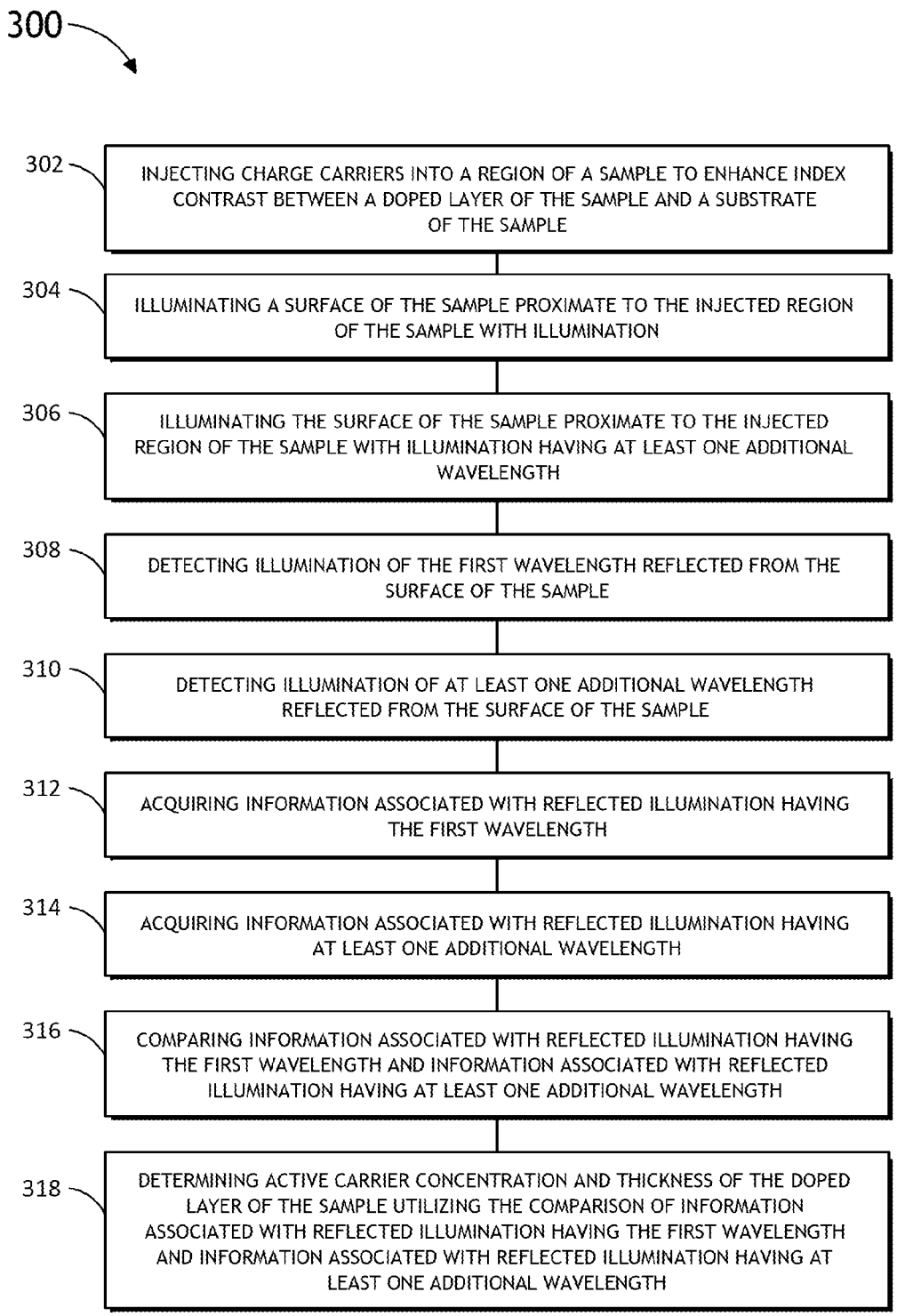
FIG. 3 is a flow diagram illustrating a method for measuring thickness and active carrier concentration of a doped semiconductor layer.
Figure 4:
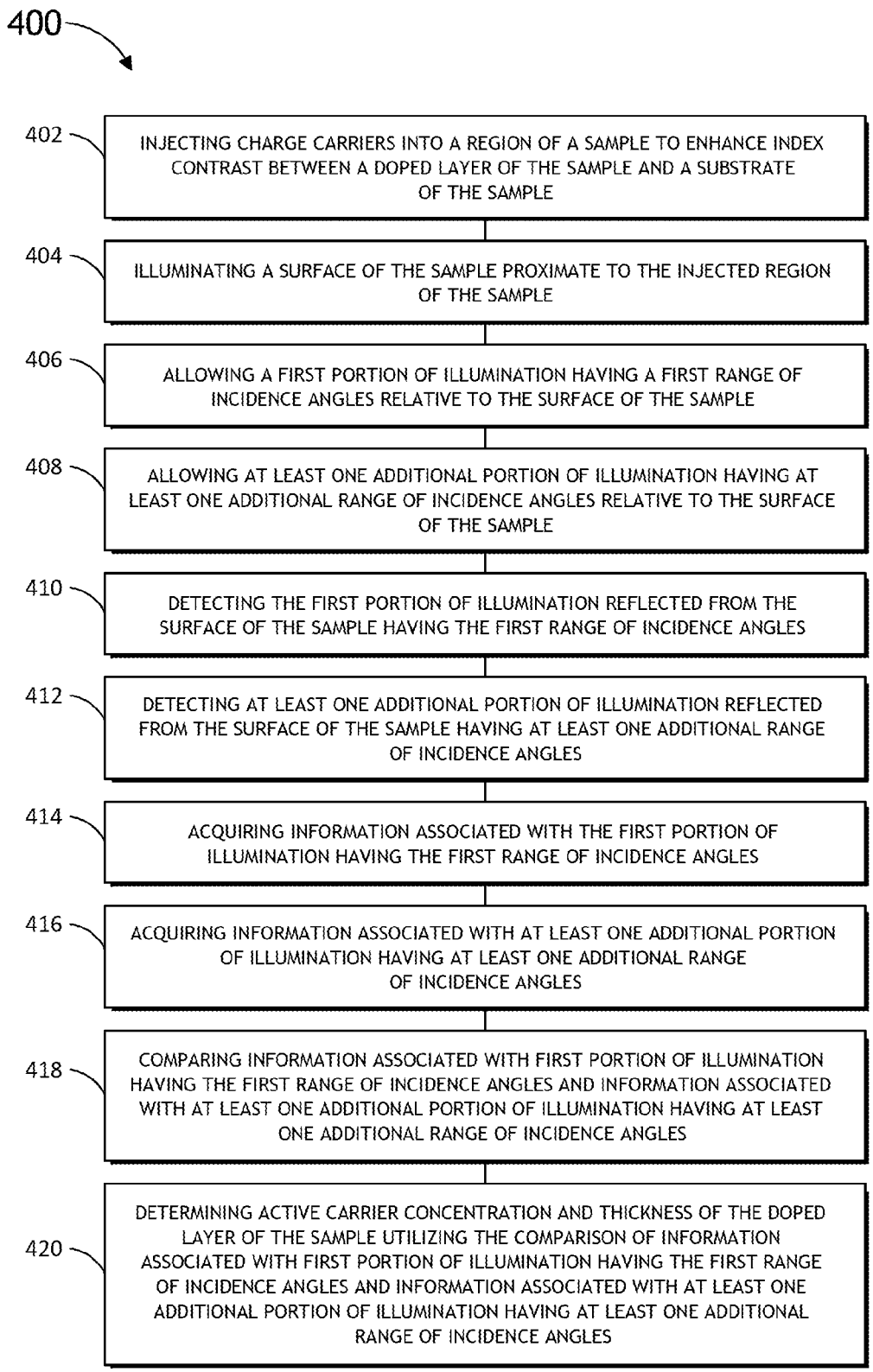
FIG. 4 is a flow diagram illustrating a method for measuring thickness and active carrier concentration of a doped semiconductor layer.

FIGS. 3 and 4 illustrate methods 300 and 400 that may be implemented by systems 100 and 200 respectively. However, it is noted herein that systems 100 and 200 are only illustrative embodiments of methods 300 and 400. Accordingly, methods 300 and 400 may encompass any technologies or techniques known to the art for carrying out the respective steps and should not be limited to the description of systems 100 and 200 included herein.

FIG. 3 is a flow diagram illustrating steps of method 300 for measuring thickness and active carrier concentration of the doped layer 104 of the sample 102 utilizing a plurality of reflectance signals measured at two or more different wavelengths.

At step 302, an electromagnetic radiation source, such as the pump source 106, may inject charge carriers into a region of the sample 102 to enhance index contrast between the doped layer 104 and the underlying substrate. The electromagnetic radiation source may also excite the region of the sample 102 periodically with intensity modulated illumination. In a further embodiment, the electromagnetic source may provide incrementally separated beams of illumination to inject charge carriers and/or excite the region of the sample 102.

At steps 304 and 306, an illumination system, such as the probe source 108, may illuminate a portion of the surface of the sample 102 proximate to the excited region. The illumination system may provide two or more portions of illumination having different wavelengths, individually or concurrently.

At steps 308 and 310, two or more portions of illumination reflected off the surface of the sample 102 having different wavelengths may be detected utilizing one or more detectors, such as the detector 110 previously described herein.

At steps 312 and 314, reflectance information may be acquired from the detected illumination. For example, information (e.g. intensity, phase, frequency, etc.) associated with two or more DC or MOR reflectance signals having different wavelengths may be acquired from the one or more detectors 110 by one or more computing systems 112.

At step 316, the acquired reflectance information for two or more reflectance signals may be compared utilizing mathematical models to define reflectance information as a function of layer thickness, active carrier concentration, and illumination wavelength. For example, information associated with a first reflectance signal having a first wavelength may be compared with an additional reflectance signal having a different wavelength. At step 318, the compared values may be utilized to identify at least one unique solution for active carrier concentration and thickness of the doped layer 104 of the sample 102.

In one embodiment, the method 300 may further include a step of determining calibration values for thickness and active carrier concentration. For example, a table of calibration values may be generated utilizing design of experiments (DOE) samples or any other control samples known to the art to carry out steps 302 through 318. Alternatively, calibration values may be determined utilizing two or more MOR signals to carry out steps 302 through 318. The method 300 may further include a sub-step of utilizing the calibration values to reduce discrepancy between measurement and model values so that the determined values for active carrier concentration and thickness of the doped layer 104 are more accurate.

FIG. 4 is a flow diagram illustrating steps of method 400 for measuring thickness and active carrier concentration of the doped layer 104 of the sample 102 utilizing a plurality of reflectance signals measured at two or more different incidence angles or ranges of incidence angles.

At step 402, an electromagnetic radiation source, such as the pump source 202, may inject charge carriers into a region of the sample 102 to enhance index contrast between the doped layer 104 and the underlying substrate. The electromagnetic radiation source may also excite the region of the sample 102 periodically with intensity modulated illumination to produce thermal waves or carrier-density modulation in the sample 102.

At step 404, an illumination system, such as the probe source 204, may illuminate a portion of the surface of the sample 102 proximate to the excited region. The illumination system may provide single-wavelength, multiple discrete wavelengths, or broad band illumination to the surface of the sample 102.

At steps 406 and 408, two or more portions of illumination may be isolated utilizing at least one discriminating optical element, such as the mask 224, so that only illumination having a desired range of incidence angles is allowed to pass. The two or more portions may be isolated to control illumination received by the detector 206 so that the detector 206 receives two or more portions of reflected illumination having different incidence angle ranges. For example, only certain portions of illumination may be allowed to pass to the surface of the sample 102 so that reflected illumination has a controlled range of incidence angles. Alternatively, only certain portions of reflected illumination having a desired range of incidence angles may be allowed to pass to the one or more detectors 206.

At steps 410 and 412, two or more portions of illumination reflected off the surface of the sample 102 having different incidence angle ranges may be detected utilizing one or more detectors, such as the detector 206 previously described herein. In one embodiment a plurality of detectors 206 may receive portions of reflected illumination having different incidence angle ranges from a plurality of optical paths defined by one or more diffractive elements.

At steps 414 and 416, reflectance information may be acquired from the detected illumination. For example, information associated with two or more MOR signals having different incidence angle ranges may be acquired from the one or more detectors 206 by one or more computing systems 208.

At step 418, the acquired reflectance information for two or more reflectance signals may be compared utilizing mathematical models to define reflectance information as a function of layer thickness, active carrier concentration, and incidence angle. For example, information associated with a first reflectance signal having a first range of incidence angles may be compared with an additional reflectance signal having a different range of incidence angles. At step 420, active carrier concentration and thickness of the doped layer 104 of the sample 102 may be determined utilizing at least one unique solution of the compared reflectance signals. In some embodiments, one or more unique solutions may be found utilizing data conditioning or approximation methods known to the art such as linear/nonlinear regression or library optimization.

In accordance with systems 100 and 200 and methods 300 and 400 discussed above, optimizations may be incorporated to improve accuracy, reduce computational time, and/or reduce the number of data points (e.g. wavelengths or angles) necessary to extract a unique solution. For example, some spatial or physical attributes of the sample 102 may be measured to acquire information (e.g. dispersion, thickness, etc.) associated with the one or more doped layers 104 of the sample 102. The spatial or physical attributes may be measured beforehand and utilized to condition or provide an improved model for subsequent thickness and active carrier concentration measurements. Alternatively, the spatial or physical attributes may be measured subsequently and utilized to condition data previously obtained about active carrier concentration of the one or more doped layers 104. The measurements taken for optimization may be obtained utilizing any metrology technique known to the art, such as X-ray, ellipsometry, or any method or device for making nondestructive measurements of physical or spatial attributes of the sample 102.

In further embodiments, the systems 100 and 200 and methods 300 and 400 may be further extended to applications in measuring ion implantation. For example, rather than measuring active carrier concentration and thickness, the foregoing systems 100 and 200 and methods 100 and 200 may be utilized under substantially the same configurations and steps, respectively, to measure damage (i.e. ion implantation) and thickness of damaged layers of a sample. The underlying techniques demonstrating applicability of the present disclosure are more fully described in U.S. Pat. Nos. 7,502,104, 7,106,446, 7,982,867, and 6,989,899, all incorporated herein by reference. In one embodiment, for example, two or more reflectance signals measured at different incidence angle ranges or at different wavelengths. The reflectance signals may be further compared utilizing a damage profile model known to the art to extract damage and thickness information of one or more damaged layers of the sample.

In the present disclosure, the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It should be recognized that the various steps described throughout the present disclosure may be carried out by a single computing system or, alternatively, a multiple computing system. Moreover, different subsystems of the system may include a computing system suitable for carrying out at least a portion of the steps described above. Therefore, the above description should not be interpreted as a limitation on the present invention but merely an illustration. Further, the one or more computing systems may be configured to perform any other step(s) of any of the method embodiments described herein.

The computing system may include, but is not limited to, a personal computing system, mainframe computing system, workstation, image computer, parallel processor, or any other device known in the art. In general, the term "computing system" may be broadly defined to encompass any device having one or more processors, which execute instructions from a memory medium.

Program instructions implementing methods such as those described herein may be transmitted over or stored on carrier medium. The carrier medium may be a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A system for analyzing at least one doped semiconductor layer, comprising:
   a pump source configured to inject charge carriers into a region of a sample to enhance index contrast between at least one doped layer of the sample and a substrate of the sample;
   one or more probe sources configured to illuminate a surface of the sample proximate to the injected region of the sample with incrementally separated beams of illumination having a first wavelength and incrementally separated beams of illumination having at least one additional wavelength;
   at least one actuation arm configured to actuate the one or more probe sources based on a disposition of incrementally separated illumination beams provided by the pump source to achieve the incremental beam separation between the incrementally separated illumination beams provided by the one or more probe sources or configured to actuate the pump source based on a disposition of the incrementally separated illumination beams provided by the one or more probe sources to achieve an incremental beam separation between one or more illumination beams provided by the pump source;

one or more detectors configured to detect illumination having the first wavelength and illumination having the at least one additional wavelength reflected from the surface of the sample; and one or more computing systems communicatively coupled to the one or more detectors, the one or more computing systems configured to:

acquire information associated with the reflected illumination having the first wavelength and information associated with the reflected illumination having the at least one additional wavelength from the one or more detectors, and determine at least one of an active carrier concentration and a thickness of the at least one doped layer of the sample based upon a comparison of the information associated with the reflected illumination having the first wavelength and the information associated with the reflected illumination having the at least one additional wavelength.

2. The system of claim 1, wherein the pump source includes a pump laser configured to inject charge carriers into the sample at a fixed power level.

3. The system of claim 1, wherein the pump source includes a pump laser configured to inject charge carriers into the sample at a plurality of discrete power levels.

4. The system of claim 1, wherein the pump source includes an intensity modulated pump laser configured to inject charge carriers into the sample at one or more discrete power levels.

5. The system of claim 1, wherein the one or more probe sources include a broad band illumination source configured to provide the illumination having the first wavelength and further configured to provide the illumination having the at least one additional wavelength.

6. The system of claim 5, wherein the broad band illumination source includes at least one of a Xenon arc lamp, a super continuum laser, or laser sustained plasma source.

7. The system of claim 1, wherein the one or more probe sources include:

a first illumination source configured to provide the illumination having the first wavelength; and at least one additional illumination source configured to provide the illumination having the at least one additional wavelength.

8. The system of claim 1, wherein the one or more computing systems are further configured to:

determine a DC reflectance of the sample utilizing the information associated with the reflected illumination having the first wavelength, determine a DC reflectance of the sample utilizing the information associated with the reflected illumination having the at least one additional wavelength, and determine the at least one of the active carrier concentration and the thickness of the at least one doped layer of the sample based upon a comparison of the DC reflectance of the sample associated with the reflected illumination having the first wavelength and the DC reflectance of the sample associated with the reflected illumination having the at least one additional wavelength.

9. The system of claim 8, wherein the one or more computing systems are further configured to:

determine modulated optical reflectance of the sample utilizing information associated with reflected illumination of each of two or more wavelengths, determine one or more calibration values for the at least one of the active carrier concentration and the thickness of the at least one doped layer of the sample based upon a comparison of the modulated optical reflectance of the sample associated with the reflected illumination of each of the two or more wavelengths, and determine the at least one of the active carrier concentration and the thickness of the at least one doped layer of the sample based upon the one or more calibration values and the comparison of the DC reflectance of the sample associated with the reflected illumination having the first wavelength and the DC reflectance of the sample associated with the reflected illumination having the at least one additional wavelength.

10. The system of claim 1, wherein the at least one actuation arm is configured to actuate the one or more probe sources based on a disposition of incrementally separated illumination beams provided by the pump source to achieve the incremental beam separation between the incrementally separated illumination beams provided by the one or more probe sources.

11. The system of claim 1, wherein the at least one actuation arm is configured to actuate the pump source based on a disposition of the incrementally separated illumination beams provided by the one or more probe sources to achieve an incremental beam separation between one or more illumination beams provided by the pump source.

12. The system of claim 1, wherein the one or more computing systems are further configured to determine the at least one of the active carrier concentration and the thickness of the at least one doped layer of the sample utilizing a mathematical model to compare the information associated with the reflected illumination having the first wavelength and the information associated with the reflected illumination having the at least one additional wavelength, wherein a difference between measured and modeled data is reduced utilizing an optimization technique including at least one of regression or library optimization.

13. The system of claim 12, wherein the mathematical model includes at least one of an Interference Model, a Drude Model, or a Soref Model.

14. The system of claim 1, further comprising:

one or more polarizing optical elements for providing metrology to the sample.

15. A method of analyzing at least one doped semiconductor layer, comprising:

injecting charge carriers into a region of a sample to enhance index contrast between at least one doped layer of the sample and a substrate of the sample;

illuminating a surface of the sample proximate to the injected region of the sample with incrementally separated beams of illumination having a first wavelength and incrementally separated beams of illumination having at least one additional wavelength, wherein the incrementally separated illumination beams are provided by one or more probe sources based on a disposition of incrementally separated illumination beams provided by a pump source;

detecting illumination having the first wavelength and illumination having the at least one additional wavelength reflected from the surface of the sample;

acquiring information associated with the reflected illumination having the first wavelength and information associated with the reflected illumination having the at least one additional wavelength; and determining at least one of an active carrier concentration and a thickness of the at least one doped layer of the sample based upon a comparison of the information associated with the reflected illumination having the first wavelength and the information associated with the reflected illumination having the at least one additional wavelength.

16. The method of claim 15, wherein the method further includes injecting charge carriers into the sample at a fixed power level.

17. The method of claim 15, wherein the method further includes injecting charge carriers into the sample at a plurality of discrete power levels.

18. The method of claim 15, wherein the method further includes:
determining a DC reflectance of the sample utilizing the information associated with the reflected illumination having the first wavelength;
determining a DC reflectance of the sample utilizing the information associated with the reflected illumination having the at least one additional wavelength;
determining the at least one of the active carrier concentration and the thickness of the at least one doped layer of the sample based upon a comparison of the DC reflectance of the sample associated with the reflected illumination having the first wavelength and the DC reflectance of the sample associated with the reflected illumination having the at least one additional wavelength.

19. The method of claim 18, wherein the method further includes:
determining modulated optical reflectance of the sample utilizing information associated with reflected illumination of each of one or more wavelengths;
determining one or more calibration values for the at least one of the active carrier concentration and the thickness of the at least one doped layer of the sample based upon a comparison of the modulated optical reflectance of the sample associated with the reflected illumination of each of the one or more wavelengths; and
determining the at least one of the active carrier concentration and the thickness of the at least one doped layer of the sample utilizing the one or more calibration values and the comparison of the DC reflectance of the sample associated with the reflected illumination having the first wavelength and the DC reflectance of the sample associated with the reflected illumination having the at least one additional wavelength.

20. The method of claim 15, wherein the method further includes:
determining the at least one of the active carrier concentration and the thickness of the at least one doped layer of the sample utilizing a mathematical model to compare the information associated with the reflected illumination having the first wavelength and the information associated with the reflected illumination having the at least one additional wavelength, wherein a difference between measured and modeled data is reduced utilizing an optimization technique including at least one of regression or library optimization.

21. The method of claim 20, wherein the mathematical model includes at least one of an Interference Model, a Drude Model, or a Soref Model.

22. The method of claim 15, wherein the method further includes:
measuring at least one spatial or physical attribute of the at least one doped layer; and
determining the at least one of the active carrier concentration and the thickness of the at least one doped layer of the sample utilizing the at least one measured spatial or physical attribute to condition the information associated with reflected illumination having the first wavelength and the information associated with reflected illumination having the at least one additional wavelength.

23. A method for analyzing at least one semiconductor layer, comprising:
injecting charge carriers into a region of a sample to enhance index contrast between at least one layer of the sample and a substrate of the sample;
illuminating a surface of the sample proximate to the injected region of the sample with incrementally separated beams of illumination having a first wavelength and incrementally separated beams of illumination having at least one additional wavelength, wherein the incrementally separated illumination beams are provided by one or more probe sources based on a disposition of incrementally separated illumination beams provided by a pump source;
detecting illumination having the first wavelength reflected from the surface of the sample and illumination having the at least one additional wavelength reflected from the surface of the sample;
acquiring information associated with the reflected illumination having the first wavelength and information associated with the reflected illumination having the at least one additional wavelength; and
determining a thickness of the at least one layer of the sample and at least one of an active carrier concentration and a damage level of the at least one layer of the sample based upon a comparison of the information associated with the reflected illumination having the first wavelength and the information associated with the reflected illumination having the at least one additional wavelength.

* * * * *